United States Patent [19]

Kalmann et al.

[11] Patent Number: 5,843,102

[45] Date of Patent: Dec. 1, 1998

[54] INSTRUMENT FOR LOOSENING AND CUTTING THROUGH THE INTIMA OF A BLOOD VESSEL, AND A METHOD THEREFOR

[75] Inventors: Menno Kalmann, Elspeet; Franciscus Laurens Moll, Bosch en Duin, both of Netherlands

[73] Assignee: Medtronic, Inc., Minneapolis, Mass.

[21] Appl. No.: 633,730

[22] PCT Filed: Oct. 18, 1994

[86] PCT No.: PCT/NL94/00254

§ 371 Date: Jun. 10, 1996

§ 102(e) Date: Jun. 10, 1996

[87] PCT Pub. No.: WO95/11633

PCT Pub. Date: May 4, 1995

[30] Foreign Application Priority Data

Oct. 25, 1993 [NL] Netherlands ............................ 9301842

[51] Int. Cl.$^6$ ..................................................... A61B 17/22
[52] U.S. Cl. .............................................................. 606/159
[58] Field of Search ..................................... 606/159, 174

[56] References Cited

U.S. PATENT DOCUMENTS

| | | | |
|---|---|---|---|
| 1,167,014 | 1/1916 | O'Brien | 606/159 X |
| 2,944,552 | 7/1960 | Cannon . | |
| 3,564,582 | 2/1971 | Wai | 606/159 X |
| 3,837,345 | 9/1974 | Matar | 606/159 |
| 4,287,890 | 9/1981 | Fogarty | 606/209 |
| 4,665,918 | 5/1987 | Garza et al. . | |
| 4,765,332 | 8/1988 | Fischell et al. | 606/159 |
| 4,994,067 | 2/1991 | Summers | 606/159 |
| 5,071,424 | 12/1991 | Reger | 606/159 |
| 5,100,423 | 3/1992 | Fearnot . | |
| 5,366,463 | 11/1994 | Ryan | 606/159 |
| 5,409,454 | 4/1995 | Fischell et al. | 606/159 X |
| 5,480,379 | 1/1996 | La Rosa . | |

FOREIGN PATENT DOCUMENTS

| | | |
|---|---|---|
| 0119688 | 9/1984 | European Pat. Off. . |
| 0274846 | 7/1988 | European Pat. Off. . |
| 2635962 | 3/1990 | France . |
| WO 90/01969 | 3/1990 | WIPO . |
| Wo 94/04096 | 3/1994 | WIPO . |

OTHER PUBLICATIONS

G. Ho, et al., "The mollring cutter™ remote endarterectomy: preliminary experience with a new endovascular technique for treatment of occlusive superficial femoral artery disease," *Journal of Endovascular Surgery,* 2(3) :278 (1995).

H. Joosten et al., "The mollring cutter™ remote endarterectomy," *Clinical Ischaemia,* 6(1) :14 (in existence as of May 30, 1996).

Remote endarterectomy using the ring strip cutter technique (in existence as of May 31, 1996).

*Primary Examiner*—Michael H. Thaler
*Attorney, Agent, or Firm*—Townsend and Townsend and Crew LLP

[57] ABSTRACT

The invention relates to an instrument for treating a blood vessel, comprising: a loosening ring of such a form as to pass between the wall of the blood vessel and the intima or tunica, which lines the inside of a blood vessel wall, for loosening the intima or tunica from the inside of the blood vessel wall; a cutting ring for cutting through and severing the loose intima at a predetermined distance within the blood vessel; and support elements for supporting the loosening and cutting rings.

17 Claims, 2 Drawing Sheets

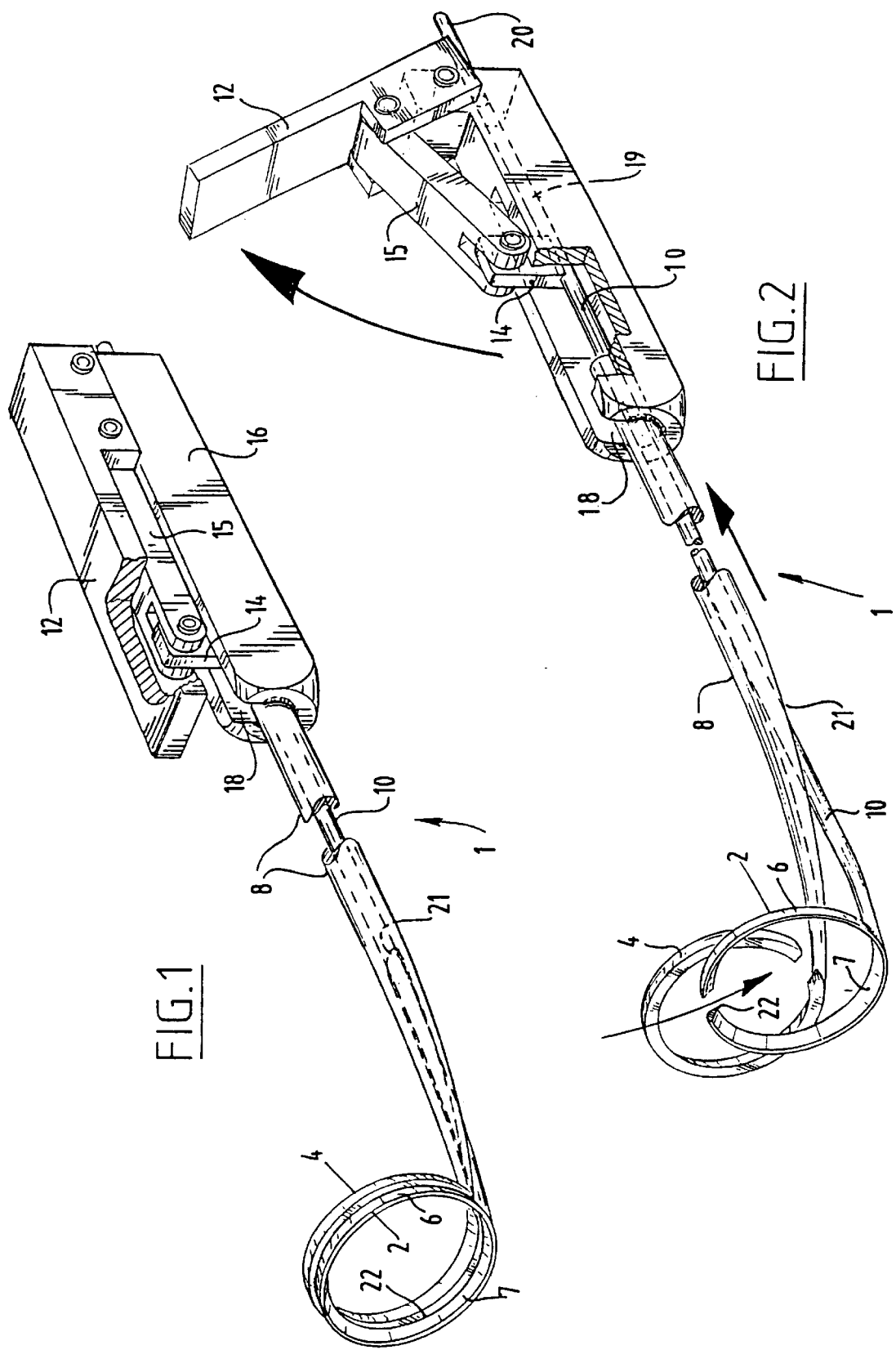

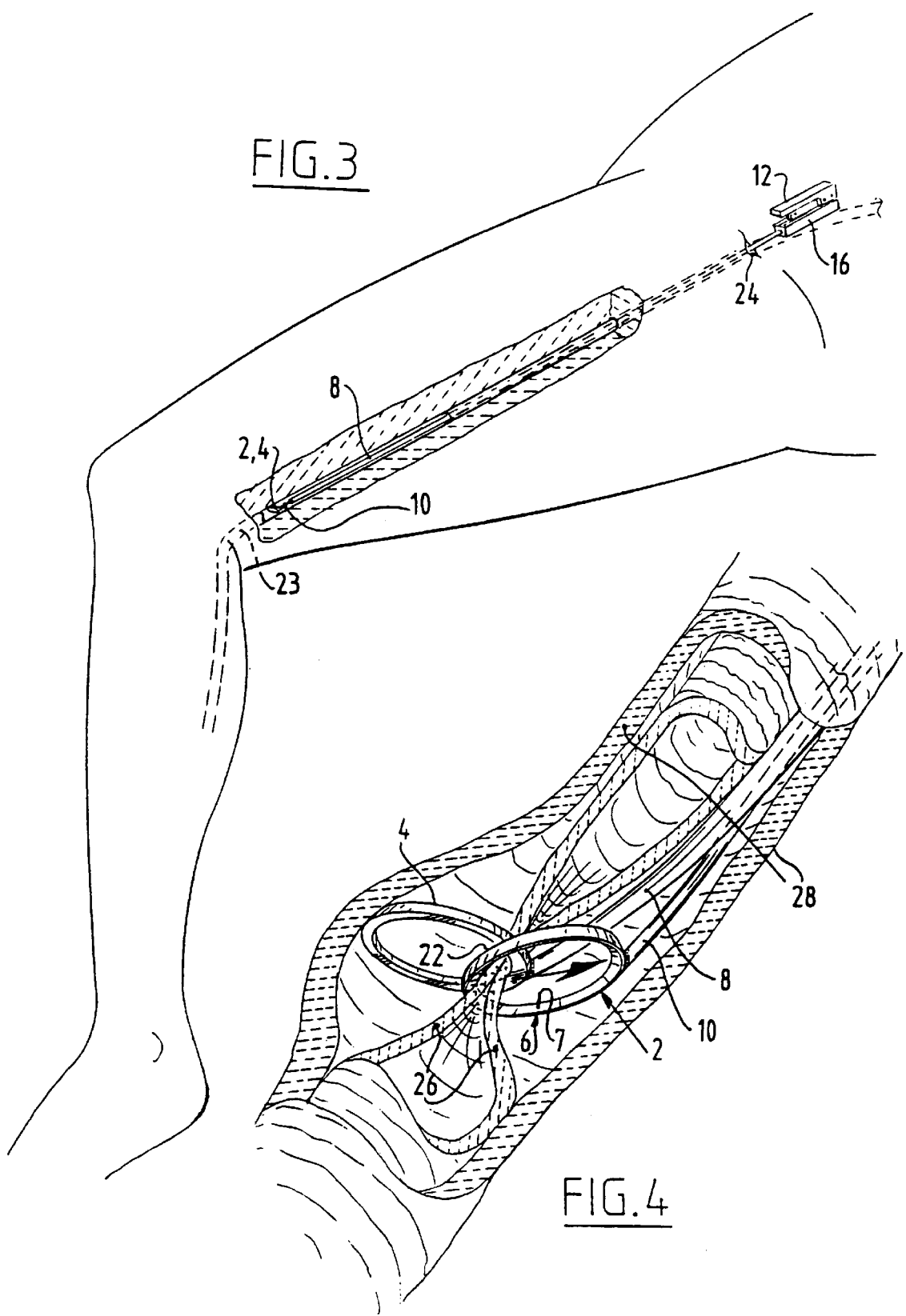

INSTRUMENT FOR LOOSENING AND CUTTING THROUGH THE INTIMA OF A BLOOD VESSEL, AND A METHOD THEREFOR

FIELD OF THE INVENTION

The present invention relates to the treatment and cleaning of blood vessels.

BACKGROUND OF THE INVENTION

It is known that narrowing or blockages (thromboses) can occur in blood vessels, particularly in older people. This is often caused by the effects of silting leading to hardening or calcifying of the blood vessels and their walls. This has dangerous consequences for the health, because the quantity of blood now able to flow through the blood vessel is drastically reduced. In order for effective blood circulation to occur and to avoid possible limb amputation for example, any blockage or obstacle in the blood vessels must be removed.

A device for the treatment of blood vessels is already known from the French patent application FR-A-2 635 962, which describes a device for completely removing varicose veins.

A complicated operation is presently necessary if hardening of the blood vessels occurs. In the case of the artery between the groin and the knee, this is quite a severe operation. The patient is cut open at the groin and the knee, whereafter the artery is completely removed and replaced by an artificial artery. This can be especially hard on and dangerous for old people particularly because of the duration of the operation. The operation is also expensive and incorporates a lengthy hospital recovery period for the patient. Additionally there is a danger of rejection of the artificial blood vessel by the body which can lead to further post operation complications.

There is thus a need for a quicker, less expensive, patient friendly procedure, for the cleaning of blood vessels, which obviates the above cited problems.

SUMMARY OF THE INVENTION

According to an aspect of the invention, an instrument is provided for treating a blood vessel comprising: loosening means of such a form as to pass between the wall of a blood vessel and the intima or tunica, which lines the inside of a blood vessel wall, for loosening the intima or tunica from the inside of the blood vessel wall; cutting through means for cutting through and severing the loose intima or tunica at a predetermined distance within the blood vessel, wherein the blood vessel wall is left substantially intact and in place; and support means for supporting the loosening and cutting means.

The intima is a sort of innertube or innerlayer which is to some extent secured to the inner side of a blood vessel wall. All blood vessel blockages are found within the intima and thus it is sufficient, in order to remove these possible blockages from the blood vessel, to cut through the intima and remove it from the blood vessel. On removing an intima, a new intima grows to replace the old one. According to the present invention an instrument is provided which via a small incision can be pushed into the blood vessel, whereby the intima is separated from the blood vessel wall. The instrument then cuts through the intima at a required distance, for example where the hardening ends, whereafter the blockage can be removed by pulling the instrument back out of the blood vessel or by any other suitable method.

A blood vessel is able to be cleaned in this manner so that the need for a time consuming, expensive operation which is harsh on the patient is removed. The requirement of an artificial replacement blood vessel is no longer present, because the old blood vessel is now in a state to again effectively fulfill its function. Therefore rejection of an artificial blood vessel by the body, and its ensuing problems, do not play a role here. The hospital recovery period is shortened due to the less exacting nature of this operation, whereby the costs decrease and more hospital beds become available.

The loosening means preferably comprise a ring part with blunt edge. The ring part preferably has a cross section in the form of a truncated cone, the nose of which projects in the direction of the incision. In this way the blunt edge separates the intima from the blood vessel wall when the instrument is pushed between the intima and the blood vessel wall. The intima is thus peeled further away from the blood vessel wall and is subjected to a sort of bottle neck effect, caused by the cone form, between the two sides of the ring.

The cutting through means preferably comprises at least two parts of such a shape that they can be inserted between the intima and the blood vessel wall, at least one part of these encircling parts being associated with moving means for moving this part with respect to the other part so that a scissor effect is obtained. These parts are preferably ring shaped, at least one of the rings having a sharp edge for cutting through the intima, and are preferably mounted at an angle next to each other at one end of the support. The supporting of the rings at an angle facilitates pushing of these parts between the intima and the blood vessel wall and reduces the probability of damage to the blood vessel wall.

The length of the support may depend on the length of the blood vessel to be cleaned and/or the extent of calcification in the blood vessel.

The moving means preferably comprises a part, that can take the form of a filament or a wire, that extends through the support and which is preferably moved with respect to the support by operating means at the opposite end of the support to the cutting through means and loosening means. The operating means preferably comprises a lever associated with the support. In this way the intima can be separated from the blood vessel wall and cut through at the required distance by the instrument which is operable from outside the body.

A grip part is preferably associated with one end of the support and a lever is associated with this grip part. In this way a secure hold on the instrument is insured for pulling the instrument back out of the blood vessel after the intima has been cut through.

The present invention also provides a method for loosening the intima or tunica from a blood vessel wall and for cutting through the intima at a certain distance, comprising: making an incision in the blood vessel, placing the instrument in the blood vessel between the blood vessel wall and the intima, moving the instrument through the blood vessel, whereby the intima is loosened from the blood vessel wall over a determined distance and cutting through and severing the intima at that distance.

The separation of the intima from the blood vessel wall and the cutting through and severing of the intima is consequently quick and able to be carried out in an elegant and simple manner. After cutting through of the intima, the intima plus blockage are removed.

Further advantages, characteristics and details of the present invention will become clear from the following description refers to the accompanying drawings, which show.

BRIEF DESCRIPTION OF THE DRAWINGS

FIG. 1 a partly broken away perspective view of an embodiment of the invention;

FIG. 2 a perspective view of the embodiment from FIG. 1, showing operation thereof;

FIG. 3 the embodiment from FIG. 1 applied to an embodiment of the method according to the present invention;

FIG. 4 is a detail of part of the embodiment from FIG. 1 in the action of cutting through an intima.

DESCRIPTION OF THE PREFERRED EMBODIMENTS

An embodiment of the instrument 1 according to the invention (FIG. 1) comprises two rings 2, 4 supported at an angle which are insertable around the intima, the front ring 2 having a blunt edge 6 and an inner, truncated conical surface 7. The second or rear ring 4 is mounted to the distal end of a hollow pin 8. The front ring 2 is mounted to the distal end of a filament 10. Filament 10 passes through and is moveable within the hollow pin 8. A projection 14 of filament 10 is connected to the lever 12 by a hinge 15. The instrument 1 also includes a grip part 16, which also acts as base for the lever 12, and a slot 18 in the grip part 16 wherein the projection 14 and the moveable part 10 extend. The hollow pin 8 is secured to the grip part 16, whilst the filament 10 moves in the slot 18. The slot 18 narrows to a narrower slot 19 (FIG. 2) which extends completely through the grip part 16.

In FIG. 2, the lever 12 is in the raised position. On raising the lever 12, the filament 10 in the hollow pin 8, is displaced to the grip part 16, via the projection 14, so that a part 20 of the moveable part 10 moves through the channel 19 and projects out from the rearside of the grip part 16. On carrying out this action the front ring 2, which is supported by the moveable part 10, moves downwards with respect to the second ring 4, so that a scissor movement is obtained between the two rings 2, 4. The filament 10 extends out of the under side of the hollow pin 8 through an opening 21, whilst on the upper side the hollow pin 8 extends to the rings 2, 4.

The blunt edge 6 of the front ring 2 extends inwardly to a sharp inner edge 22 of the front ring 2 (FIGS. 1 and 2).

An instrument 1 according to the invention is inserted into the artery 23, see FIG. 3, via a small incision 24 of about 8–10 cm in the groin, between the groin and the knee, in such a way that the rings 2, 4 extend in the direction of the knee whilst the lever 12 and the grip part 16 are located outside of the body, near to the incision 24 of the artery 23.

The front ring 2 is moved downwards with respect to the rear ring 4, by the scissor movement of the two rings 2, 4 (FIG. 4), causing the intima 26, which is already separated from the blood vessel wall 28 to be pinched between the two rings 2, 4. It is clear that further downwards movement of the front ring 2 will result in the cutting through and severing of the intima 26 which is held between the sharp edge 22 of the front ring 2, supported by the hollow pin 8, and the rear ring 4, supported by the moveable part of filament 10.

The rings 2, 4 are preferably sharpened for about 40%, or 144° of their contours, front ring 2 sharpened along its upper inner side and rear ring 4 sharpened along its lower inner side, in order to achieve a highly efficient shear, scissor-like cutting movement when front ring 2 is moved relative to rear ring 4. This scissor-like cutting effect is particularly efficient in cutting through hardened, calcified material as relatively little mechanical force is needed in operation of the instrument, to effect a neat cut.

The rings 2, 4 are flattened where they meet, as shown in FIG. 2, in order to fit together as a single ring so that no obstructions project which could damage the outer layer of the blood vessel during insertion, operation and/or removal of the instrument.

From clinical tests it has been determined that an effective cutting through and severing is achieved when the rings are mounted at an angle of 45° relative to the filament and hollow pin. However it will be obvious that the rings could be mounted in any direction and in any relative position in order to achieve efficient cutting.

At this angle of 45° it was found that the following ring diameters, with respect to the inner diameter of the blood vessel, yielded efficient separation of the intima from the blood vessel wall and cutting through and severing of the intima and any hardened, calcified material therein.

| Inner diameter blood vessel | diameter rings |
|---|---|
| 4 mm | 6,5 mm |
| 5 mm | 7,5 mm |
| 6 mm | 8,5 mm |

On inserting the instrument into an already opened blood vessel (FIGS. 3, 4) the front ring 2 and the rear ring 4 encircle the intima 26. The instrument is then pushed through the blood vessel. The blunt edge 6 of the front ring 2 separating the intima from the blood vessel wall 28, whereby the intima 26 is forced further inwards away from the blood vessel wall by a funnel effect brought about by the front ring 2. After the two rings 2, 4 have been moved to a required distance in the blood vessel, for instance to a point where there is no more blockage of the blood vessel, the movement is stopped and the lever 12 is raised which brings about the earlier stated scissor movement for the cutting through and severing of the intima.

In order to further improve cutting and severing, at least one of the rings, preferably the front ring 2, may be vibrated during the scissor movement.

The intima and the blockage therein can be removed either by removing the instrument from the blood vessel or by any other way.

It will be noted that the present invention is not limited to the embodiment as herein drawn and described, for instance in a further (not shown) embodiment of the present invention the filament and hollow pin may be reversed so that the filament extends out of an opening on the upperside of the hollow pin, the position of the filament's and hollow pin's respective rings being reversed, whereupon cutting is achieved by pushing the filament instead of pulling the filament, and in yet another (not shown) embodiment of the present invention, the hollow pin may be pushed to achieve a cutting movement, instead of pulling the filament.

A further advantage of the present invention is that blocked blood vessels, specifically the artery between the groin and the knee, can be unblocked to allow the insertion, via this artery, of a prosthetic into the aorta to treat patients who, along with blocked blood vessels, also have aneurisms for instance. For these patients the chest now no longer has to be opened in order to treat the aneurism, as the now, unblocked artery between the knee and the groin yields a prosthetic access to the aorta.

A large number of modifications and variations are conceivable within the range of the following claims.

We claim:

1. An instrument for treating a blood vessel comprising:
   means for loosening the intima or tunica which lines the inside of a blood vessel wall from the blood vessel wall, the means for loosening comprising an open-ended loosening ring having a longitudinal axis;
   a second ring;
   means for cutting through the intima or tunica passing through the rings;
   means for supporting the loosening ring;
   means for supporting the second ring; and
   means for moving the rings with respect to each other along a path transverse to the longitudinal axis of the loosening ring through the relative movement of the means for supporting the loosening and second rings thereby causing the cutting means to cut the intima or tunica passing through the rings.

2. The instrument according to claim 1, wherein the second ring is mounted on the means for supporting the rings adjacent to the loosening ring and between the means for operating the means for moving the rings and the loosening ring.

3. The instrument according to claim 1 wherein the rings are substantially circular in cross-section.

4. The instrument according to claim 1 wherein the means for moving the rings comprises a filament, the means for supporting the rings comprises a substantially circular in cross-section hollow pin, wherein the pin houses the filament.

5. The instrument according to claim 4, wherein the loosening ring is mounted on the filament.

6. The instrument according to claim 5, wherein the second ring is mounted on the hollow pin.

7. The instrument according to claim 4, wherein the means for operating the means for moving the rings comprises a lever engaged with the filament or the hollow pin.

8. The instrument according to claim 7, wherein the loosening ring has a truncated conical surface narrowing in the direction of the means for moving the rings.

9. The instrument according to claim 8, wherein the loosening ring comprises a blunt leading edge.

10. The instrument according to claim 9, wherein the rear edge of the loosening ring and the front edge of the second ring are substantially flattened, so that the two rings fit together as a substantially single ring section.

11. The instrument according to claim 1 further comprising a grip part encaged with one end of the means for supporting the rings.

12. A method for loosening the intima from a blood vessel and for cutting through and severing the intima at a determined distance comprising:
   making an incision in the blood vessel;
   placing an instrument in the blood vessel between the blood vessel wall and the intima;
   moving the instrument through the blood vessel to a distal position, whereby the intima is loosened from the blood vessel wall over a determined distance;
   cutting through and severing the intima from the blood vessel wall at the distal position without the need to make a second incision in the blood vessel;
   said cutting through and severing step carried out using an instrument within the blood vessel; and
   wherein the instrument placing step is carried out using an instrument comprising means for loosening the intima or tunica which lines the inside of a blood vessel wall from the blood vessel wall, the means for loosening comprising a loosening ring having a longitudinal axis; a second ring; means for cutting through the intima or tunica passing through the rings; means for supporting the loosening ring; means for supporting the second ring; and means for moving the rings with respect to each other along a path transverse to the longitudinal axis of the loosening ring through the relative movement of the means for supporting the loosening and second rings.

13. The method according to claim 12 wherein the intima cutting and severing step is carried out using elongate members with distal ends, the loosening and second rings being located on the distal ends of the elongate members such that moving the elongate members relative to one another moves the loosening ring relative to the second ring thereby cutting the intima or tunica passing through the rings.

14. An instrument for treating a blood vessel comprising:
   a base assembly;
   first and second elongate members, each of the elongate members having a proximal end and a distal end defining a length therebetween, the proximal ends of the elongate members mounted to the base assembly;
   an open-ended loosening ring attached to the distal end of the first elongate member for loosening a length of intimal lining of a blood vessel from the blood vessel wall;
   a cutting ring attached to the distal end of the second elongate member; and
   means for moving the loosening and cutting rings relative to one another along a cutting path transverse to the lengths of the elongate members from an aligned orientation to an offset orientation to sever any tissue passing through the rings.

15. The instrument according to claim 14 wherein the loosening ring and the cutting ring are substantially circular in cross-section.

16. The instrument according to claim 14 wherein the loosening ring tapers to form a truncated conical surface narrowing in the direction of the proximal ends of the elongate members.

17. The instrument according to claim 16 wherein portions of the loosening ring and cutting ring are substantially flattened, abutting surfaces, so that the loosening ring and the cutting ring fit together to form a single ring structure when in the aligned orientation.

* * * * *